US006635645B1

(12) United States Patent
Lochead et al.

(10) Patent No.: US 6,635,645 B1
(45) Date of Patent: Oct. 21, 2003

(54) 2,5,-DIAZABICYCLO[2.2.1]HEPTANE DERIVATIVES, THEIR PREPARATION AND THERAPEUTIC USES

(75) Inventors: Alistair Lochead, Charenton (FR); Samir Jegham, Montferrier sur Lez (FR); Alain Nedelec, Colombes (FR); Jean Jeunesse, Paris (FR); Frédéric Galli, Vaucresson (FR); Luc Even, Paris (FR)

(73) Assignee: Sanofi-Synthelabo, Paris (FR)

( * ) Notice: Subject to any disclaimer, the term of this patent is extended or adjusted under 35 U.S.C. 154(b) by 0 days.

(21) Appl. No.: 09/856,946

(22) PCT Filed: Dec. 1, 1999

(86) PCT No.: PCT/FR99/02974

§ 371 (c)(1), (2), (4) Date: Aug. 16, 2001

(87) PCT Pub. No.: WO00/34284

PCT Pub. Date: Jun. 15, 2000

(30) Foreign Application Priority Data

Dec. 4, 1998 (FR) ............................................. 98 15325

(51) Int. Cl.$^7$ ....................... C07D 487/08; A61K 31/44; A61K 31/501; A61K 31/506; A61P 25/28

(52) U.S. Cl. ............................. 514/252.01; 514/252.04; 514/252.11; 514/256; 514/269; 546/238; 546/330; 546/349; 546/357; 546/359; 546/360

(58) Field of Search ................................. 544/238, 330, 544/320, 359, 360, 349, 357; 514/256, 269, 252.14, 247, 252.01, 252.11, 252.04

(56) References Cited

U.S. PATENT DOCUMENTS

| 4,954,502 A | * | 9/1990 | Smith et al. ................. 544/364 |
| 4,994,460 A | * | 2/1991 | Dextraze et al. ............. 544/295 |
| 5,478,939 A | * | 12/1995 | Trybulski et al. ........... 514/336 |

OTHER PUBLICATIONS

Clementi et al.European Journal of Pharmacology, 393, Mar. 10, 2000.*

* cited by examiner

*Primary Examiner*—Mukund J. Shah
*Assistant Examiner*—Venkataraman Balasubramanian
(74) *Attorney, Agent, or Firm*—Michael D. Alexander

(57) ABSTRACT

The invention relates to 2,5-diazabicyclo[2.2.1]heptane derivatives, to pharmaceutical compositions containing them, and to methods for the treatment or prevention of disorders associated with a dysfunction of the nicotinic receptors utilizing them.

5 Claims, No Drawings

2,5,-DIAZABICYCLO[2.2.1]HEPTANE DERIVATIVES, THEIR PREPARATION AND THERAPEUTIC USES

The compounds of the present invention correspond to the general formula (I)

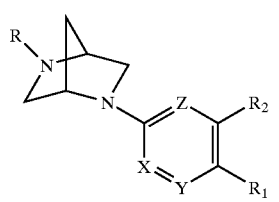

(I)

in which one of the symbols X, Y and Z represents a nitrogen atom, another represents a group of formula C—$R_3$ and the third represents a nitrogen atom or a group of formula C—$R_4$, $R_3$ and $R_4$ represent, independently of each other, a hydrogen or halogen atom or a trifluoromethyl, cyano, hydroxyl, ($C_1$–$C_6$)alkyl or ($C_1$–$C_6$)alkoxy group, $R_1$ and $R_2$ represent, independently of each other, a hydrogen or halogen atom or a trifluoromethyl, cyano, hydroxyl, ($C_1$–$C_6$)alkyl or ($C_1$–$C_6$)alkoxy group, or a phenyl group optionally substituted with one or two halogen atoms, with one or two trifluoromethyl groups, with a cyano group, with a nitro group, with a hydroxyl group, with a ($C_1$–$C_6$)alkyl group, with one or two Scheme

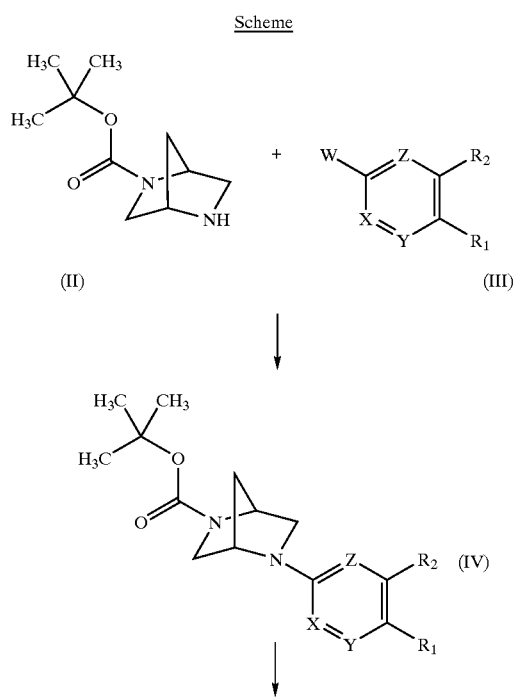

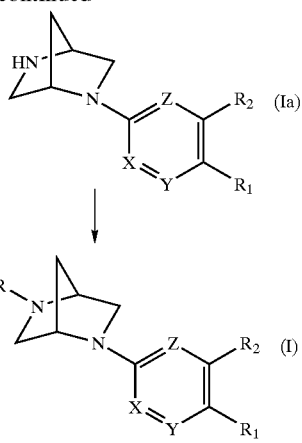

($C_1$–$C_6$)alkoxy groups, with a methylenedioxy group, with an acetyl group, with a trifluoromethoxy group or with a methylthio group, R represents a hydrogen atom or a ($C_1$–$C_6$)alkyl group, with the exclusion, however, of the compounds of general formula (I) in which X represents a group of formula CH, Y and Z each represent a nitrogen atom, and $R_1$ or $R_2$ does not represent an optionally substituted phenyl group.

The compounds thus excluded are described in U.S. Pat. No. 5,478,939 as muscarine agonists.

The compounds of the invention can exist in the form of bases or of addition salts with acids. They can also exist in the form of (S,S) or (R,R) isomers.

The preferred compounds are those in the formula of which the heterocycle containing X, Y and Z is a 3-pyridyl or 3-pyridazinyl group.

In accordance with the invention, and according to the preceding scheme, the compounds of general formula (I) can be prepared by reacting 1,1-dimethylethyl 2,5-diazabicyclo [2.2.1]heptane-2-carboxylate of formula (II) with a heterocyclic compound of general formula (III), in which X, Y, Z, $R_1$ and $R_2$ are as defined above and W represents a halogen atom.

Thus, it is possible to carry out a Buchwald coupling (J. Org. Chem. (1997) 62 6066–6068) in the presence of a palladium catalyst such as palladium acetate, tris(dibenzylideneacetone)dipalladium(0), etc., of a complexation ligand such as triphenylphosphine, tributylphosphine or 2,2'-bis(diphenylphosphino)-1,1'-binaphthyl, and of a base, for example an organic base such as sodium t-butoxide, or an inorganic base such as caesium carbonate.

When X or Z represents a nitrogen atom, it is also possible to carry out a standard nucleophilic substitution reaction in the presence of a strong base such as caesium carbonate or triethylamine.

A compound of general formula (IV) is obtained, in which, if so desired, it is possible to modify the substituents $R_1$ or $R_2$; for example, when $R_1$ or $R_2$ represents a halogen atom, it can be substituted with an alkyl or phenyl group by a Suzuki reaction, using an alkylboronic or phenylboronic acid, in the presence of tetrakis(triphenylphosphine) palladium.

The compound of general formula (IV) is then deprotected in a known manner, for example using trifluoroacetic acid or hydrochloric acid, to give a compound of general formula (Ia), which corresponds to the general formula (I) when R represents a hydrogen atom.

It is then possible, if so desired, to carry out an alkylation of this compound, either by a reductive amination (formaldehyde and sodium cyanoborohydride) or by an Eschweiler-Clarke reaction (formaldehyde and formic acid).

1,1-Dimethylethyl (1S)-diazabicyclo[2.2.1]heptane-2-carboxylate of formula (II) is described in *J. Org. Chem.* (1988) 53 1580–1582 and 1,1-dimethylethyl (1R)-diazabicyclo[2.2.1]heptane-2-carboxylate of formula (II) is described in patent application EP-400,661.

The compounds of general formula (III) are commercially available or are accessible by methods described in the literature.

The examples which follow illustrate the preparation of a number of compounds of the invention. The elemental microanalyses and the IR and NMR spectra confirm the structures of the compounds obtained.

The numbers indicated in parentheses in the example titles correspond to those in the first column of Table 1 given later.

In the compound names, the hyphen "-" forms part of the name, and the underscore line "_" serves merely to indicate the line break; it should be removed if a line break does not occur at that point, and should not be replaced either with a normal hyphen or with a space.

EXAMPLE 1

Compound 2

(1S)-2-(6-Chloro-3-pyridyl)-2,5-diazabicyclo[2.2.1]heptane Hydrochloride (2:1)

1.1. 1,1-Dimethylethyl (1S)-2-(6-chloro-3-pyridyl)-2,5-diazabicyclo[2.2.1]heptane-5-carboxylate and 1,1-dimethylethyl (1S)-2-(5-bromo-2-pyridyl)-2,5-diazabicyclo[2.2.1]heptane-5-carboxylate 4.96 g (25 mmol) of 1,1-dimethylethyl (1S)-2,5-diazabicyclo[2.2.1]heptane-5-carboxylate, 5.0 g (26 mmol) of 5-bromo-2-chloropyridine and 11.4 g (35 mmol) of caesium carbonate suspended in 150 ml of tetrahydrofuran are placed into a 500 ml three-necked round-bottomed flask, a stream of nitrogen is bubbled through for 15 min, 224 mg (1.0 mmol) of palladium(II) acetate and 623 mg (1.0 mmol) of 2,2'-bis(diphenylphosphino)-1,1'-binaphthyl are added and the mixture is refluxed for 22 h.

This mixture is filtered, the solvent is evaporated off and the residue is purified by chromatography on a column of silica gel, eluting with a 40/60 mixture of ethyl acetate and heptane. 1.63 g of 1,1-dimethylethyl (1S)-2-(5-bromo-2-pyridyl)-2,5-diazabicyclo[2.2.1]heptane-5-carboxylate, melting point: 181–182° C., $[\alpha]_D^{20}=-229.4°$ (c=1, $CH_2Cl_2$), and 3.65 g of 1,1-dimethylethyl (1S)-2-(6-chloro-3-pyridyl)-2,5-diazabicyclo[2.2.1]heptane-5-carboxylate, melting point: 189° C., $[\alpha]_D^{20}=-224.5°$ (c=1, $CH_2Cl_2$), are obtained.

1.2. (1S)-2-(6-Chloro-3-pyridyl)-2,5-diazabicyclo[2.2.1]heptane Hydrochloride (2:1)

3.0 g (9.71 mmol) of 1,1-dimethylethyl (1S)-2-(6-chloro-3-pyridyl)-2,5-diazabicyclo[2.2.1]heptane-5-carboxylate are dissolved in 250 ml of ethyl acetate in a 500 ml three-necked round-bottomed flask and a stream of gaseous hydrogen chloride is bubbled through for 30 min.

The solvent is evaporated off under reduced pressure, the residue is taken up in 25 ml of ethyl acetate and the solid is collected by filtration and recrystallized from 25 ml of ethanol.

2.39 g of dihydrochloride are obtained.

Melting point: 290–300° C., $[\alpha]_D^{20}=-105.6°$ (c=0.5, $H_2O$)

EXAMPLE 2

Compound 4

(1S)-2-(6-Chloro-3-pyridyl)-5-methyl-2,5-diazabicyclo[2.2.1]heptane (E)-but-2-Enedioate (2:1)

0.55 g (2.65 mmol) of (1S)-2-(6-chloro-3-pyridyl)-2,5-diazabicyclo[2.2.1]heptane dissolved in 20 ml of ethanol is placed into a 100 ml three-necked round-bottomed flask, the solution is cooled to 0° C., 0.43 ml (5.31 mmol) of aqueous 37% formaldehyde solution is added slowly, followed by portionwise addition of 0.334 g (5.31 mmol) of sodium cyanoborohydride, while keeping the temperature close to 0° C., and stirring is continued for 30 min.

The mixture is diluted with water and extracted with chloroform, the organic phase is evaporated under reduced pressure and the residue is purified by chromatography on a column of silica gel, eluting with a 95/5/0.5 mixture of dichloromethane, methanol and aqueous ammonia.

0.290 g of compound is obtained in the form of a base.

0.258 g of this product is dissolved in 20 ml of ethanol, the solution is treated with 0.134 g of fumaric acid, the solvent is evaporated off under reduced pressure and the solid is collected by filtration.

0.292 g of fumarate is finally isolated.

Melting point: 143.6° C., $[\alpha]_D^{20}=-94.5°$ (c=0.5, $H_2O$)

EXAMPLE 3

Compound 6

(1S)-2-(6-Chloro-3-pyridazinyl)-2,5-diazabicyclo[2.2.1]heptane Hydrochloride (2:1)

3.1. 1,1-Dimethylethyl (1S)-2-(6-Chloro-3-pyridazinyl)-2,5-diazabicyclo[2.2.1]heptane-5-carboxylate 0.397 g (2.0 mmol) of 1,1-dimethylethyl (1S)-2,5-diazabicyclo[2.2.1]heptane-5-carboxylate, 0.328 g (2.2 mmol) of 3,6-dichloropyridazine and 1.3 g (4 mmol) of caesium carbonate in 30 ml of toluene are placed into a 100 ml three-necked round-bottomed flask and the mixture is refluxed for 48 h.

This mixture is filtered, the solvent is evaporated off under reduced pressure and the residue is purified by chromatography on a column of silica gel, eluting with an 80/20 mixture of ethyl acetate and heptane.

0.3 g of compound is obtained.

Melting point: 198° C.

3.2. (1S)-2-(6-Chloro-3-pyridazinyl)-2,5-diazabicyclo[2.2.1]heptane Hydrochloride (2:1)

0.25 g (0.933 mmol) of 1,1-dimethylethyl (1S)-2-(6-chloro-3-pyridazinyl)-2,5-diazabicyclo[2.2.1]heptane-5-carboxylate and 20 ml of ethyl acetate are placed into a 50 ml three-necked round-bottomed flask, gaseous hydrogen chloride is bubbled through for 10 min and stirring is continued for 30 min.

The solvent is evaporated off under reduced pressure, the residue is taken up in 5 ml of ethyl acetate and the solid is collected by filtration, rinsed with ethyl acetate and dried.

0.155 g of hydrochloride is obtained.

Melting point: 260–270° C., $[\alpha]_D^{20}=-99.5°$ (c=0.5, $H_2O$)

EXAMPLE 4

Compound 7

(1S)-2-(6-Phenyl-3-pyridazinyl)-2,5-diazabicyclo[2.2.1]heptane 4.1. 1,1-Dimethylethyl (1S)-2-(6-Phenyl-3-pyridazinyl)-2,5-diazabicyclo[2.2.1]heptane-5-carboxylate 1.0 g (5.0 mmol) of 1,1-dimethylethyl (1S)-2,5-diazabicyclo[2.2.1]heptane-2-carboxylate, 1.14 g (6.0 mmol) of 3-chloro-6-phenylpyridazine and 0.84 ml (6.0 mmol) of triethylamine in 45 ml of toluene are introduced into a 100 ml three-necked round-bottomed flask and the mixture is refluxed for 72 h.

The reaction medium is diluted with water, the organic phase is separated out and the solvent is evaporated off under reduced pressure. The residue is purified by chromatography on silica gel, eluting with a 90/10 mixture of dichloromethane and acetone. 0.96 g of product is thus obtained, which is triturated in diisopropyl ether to isolate 0.92 g of pure product after drying.

Melting point: 208–209° C.

4.2. (1S)-2-(6-Phenyl-3-pyridazinyl)-2,5-diazabicyclo[2.2.1]heptane 0.9 g (2.55 mmol) of (1S)-2-(6-phenyl-3-pyridazinyl)-2,5-diazabicyclo[2.2.1]heptane-5-carboxylate and 25 ml of ethyl acetate are placed in a 100 ml three-necked round-bottomed flask, gaseous hydrogen chloride is bubbled through for 10 min and stirring is continued for 30 min.

The solvent is evaporated off under reduced pressure and the residue is taken up in aqueous potassium hydroxide solution and extracted with chloroform. The chloroform phase is evaporated and the residue obtained is triturated in diisopropyl ether to give 0.59 g of pure product.

Melting point: 162–163° C., $[\alpha]_D^{20}$=–187.8° (c=0.5, CHCl$_3$)

EXAMPLE 5

Compound 8

(1S)-2-(6-Phenyl-3-pyridazinyl)-5-methyl-2,5-diazabicyclo[2.2.1]heptane 0.439 g (1.74 mmol) of (1S)-2-(6-phenyl-3-pyridazinyl)-2,5-diazabicyclo[2.2.1]heptane dissolved in 15 ml of ethanol and 0.21 ml (3.48 mmol) of acetic acid are placed in a 100 ml three-necked round-bottomed flask. 0.284 ml (3.48 mmol) of an aqueous formaldehyde solution is added, followed by portionwise addition of 0.218 g (3.48 mmol) of sodium cyanoborohydride, while keeping the temperature at about 5° C., and stirring is continued for 1 h.

The reaction medium is diluted with water, aqueous potassium hydroxide solution is added and this mixture is extracted with chloroform. The organic phase is evaporated under reduced pressure and the residue obtained is purified by chromatography on a column of silica gel, eluting with a 97/3/0.3 mixture of chloroform, methanol and aqueous ammonia.

0.430 g of product is thus obtained, which is triturated in hot diisopropyl ether to isolate, after drying, 0.392 g of compound.

Melting point: 112.6–113° C., $[\alpha]_D^{20}$=–165.3° (c=0.5, CHCl$_3$)

EXAMPLE 6

Compound 9

(1S)-2-(5-Phenyl-3-pyridyl)-2,5-diazabicyclo[2.2.1]heptane 6.1. 1,1-Dimethylethyl (1S)-2-(5-Bromo-3-pyridyl)-2,5-diazabicyclo[2.2.1]heptane-5-carboxylate 1.98 g (10 mmol) of 1,1-dimethylethyl (1S)-2,5-diazabicyclo[2.2.1]heptane-2-carboxylate, 7.1 g (30 mmol) of 3,5-dibromopyridine and 4.56 g (14 mmol) of caesium carbonate suspended in 100 ml of tetrahydrofuran are placed in a 250 ml three-necked round-bottomed flask, a stream of nitrogen is bubbled through for 15 min, 90 mg (0.4 mmol) of palladium diacetate and 249 mg (0.4 mmol) of 2,2'-bis(diphenylphosphino)-1,1'-binaphthyl are added and the reaction mixture is refluxed for 22 h.

The reaction medium is filtered and the filtrate is concentrated under reduced pressure. The residue obtained is purified by chromatography on silica gel, eluting with a 40/60 mixture of ethyl acetate and heptane.

2.99 g of 1,1-dimethylethyl (1S)-2-(5-bromo-3-pyridyl)-2,5-diazabicyclo[2.2.1]heptane-5-carboxylate are thus obtained.

Melting point: 149° C., $[\alpha]_D^{20}$=–196.5° (c=0.5, CH$_2$Cl$_2$)

6.2. 1,1-Dimethylethyl (1S)-2-(5-Phenyl-3-pyridyl)-2,5-diazabicyclo[2.2.1]heptane-5-carboxylate 8 ml of benzene, 147 mg (0.127 mmol) of tetrakis(triphenylphosphine)palladium and 1.5 g (4.23 mmol) of 1,1-dimethylethyl (1S)-2-(5-bromo-3-pyridyl)-2,5-diazabicyclo[2.2.1]heptane-5-carboxylate are placed, under argon, in a 25 ml three-necked round-bottomed flask, 4 ml of aqueous 2 M sodium carbonate solution, 0.568 g (4.66 mmol) of phenylboronic acid and 0.2 ml of ethanol are added and the mixture is refluxed for 3 h.

The reaction medium is allowed to separate by settling and the organic phase is chromatographed on silica gel, eluting with a 75/25 and then 90/10 mixture of ethyl acetate and heptane.

1.55 g of compound are obtained, which product is triturated in hot diisopropyl ether to isolate 1.36 g of product.

Melting point: 163.5–164° C., $[\alpha]_D^{20}$=–194.9° (c=0.5, CH$_2$Cl$_2$)

6.3. (1S)-2-(5-Phenyl-3-pyridyl)-2,5-diazabicyclo[2.2.1]heptane 1.30 g (3.7 mmol) of 1,1-dimethylethyl (1S)-2-(5-phenyl-3-pyridyl)-2,5-diazabicyclo[2.2.1]heptane-5-carboxylate dissolved in 40 ml of ethyl acetate are placed in a 100 ml three-necked round-bottomed flask, gaseous hydrogen chloride is bubbled through for 30 min and the solvent is then evaporated off.

The reaction medium is basified with aqueous ammonia and extracted with chloroform. The solvent is evaporated off and the residue is triturated in diethyl ether.

0.438 g of pure compound is thus obtained.

Melting point: 116–117° C., $[\alpha]_D^{20}$–134.9 (c=0.5, CH$_2$Cl$_2$)

EXAMPLE 7

Compound 15

(1S)-2-(6-Phenyl-3-pyridyl)-2,5-diazabicyclo[2.2.1]heptane 7.1. 3-Bromo-6-phenylpyridine 10 g (42.2 mmol) of 2,5-dibromopyridine, 5.2 g (42.2 mmol) of phenylboronic acid and 30 ml of benzene are placed in a 250 ml three-necked round-bottomed flask, 1.5 g (1.3 mmol) of tetrakis(triphenylphosphine)palladium, 30 ml of benzene and 30 ml of aqueous 2 M sodium carbonate solution and 1.4 ml of ethanol are added and the mixture is refluxed for 17 h.

The reaction medium is cooled and filtered, the organic phase is separated out by settling, the solvent is evaporated off under reduced pressure and the residue is purified by chromatography on silica gel, eluting with a 70/30 mixture of heptane and dichloromethane.

8.6 g of crude product are obtained, which product is recrystallized from 7 ml of ethanol. 5.6 g of pure product are thus obtained in the form of a white solid.

Melting point: 69–72° C.

7.2. 1,1-Dimethylethyl (1S)-2-(6-Phenyl-3-pyridyl)-2,5-diazabicyclo[2.2.1]heptane-5-carboxylate 40 ml of tetrahydrofuran, 1.59 g (8.0 mmol) of 1,1-dimethylethyl (1S)-2,5-diazabicyclo[2.2.1]heptane-2- carboxylate, 2.25 g (9.6 mmol) of 3-bromo-6-phenylpyridine, 3.65 g (11.2 mmol) of caesium carbonate, 72 mg of palladium diacetate and 0.20 g (0.32 mmol) of 2,2'-bis(diphenylphosphino)-1,1'-binaphthyl are placed, under nitrogen, in a 100 ml three-necked round-bottomed flask and the mixture is refluxed for 18 h.

This mixture is filtered, the solvent is evaported off under reduced pressure and the residue is purified by chromatography on silica gel, eluting with a 40/60 mixture of ethyl acetate and heptane, to give 2.9 g of crude product, which product is triturated in diisopropyl ether.

2.4 g of pure product are thus obtained.

Melting point: 147.5° C., $[\alpha]_D^{20}$=−251.3 (c=0.5, $CH_2Cl_2$)

7.3. (1S)-2-(6-Phenyl-3-pyridyl)-2,5-diazabicyclo[2.2.1]heptane 2.3 g (6.8 mmol) of 1,1-dimethylethyl (1S)-2-(6-phenyl-3-pyridyl)-2,5-diazabicyclo[2.2.1]heptane-5-carboxylate dissolved in 100 ml of ethyl acetate are placed in a 250 ml three-necked round-bottomed flask and gaseous hydrogen chloride is bubbled through for 30 min.

The solvent is evaporated off under reduced pressure and the residue is triturated in ether. The residue is basified by addition of aqueous sodium hydroxide solution and is extracted with chloroform. The solvent is evaporated off under reduced pressure to give 1.7 g of solid, which product is triturated in diisopropyl ether. 1.52 g of product are thus obtained in the form of a white solid.

Melting point: 121.5–122° C., $[\alpha]_D^{20}$=−178.7° (c=0.5, $CH_2Cl_2$)

The table which follows illustrates the chemical structures and physical properties of a number of compounds of the invention. In the "Salt" column, "-" denotes a compound in base form, "HBr" denotes a hydrobromide, "HCl" denotes a hydrochloride, "fum" denotes a fumarate, or (E)-but-2-enedioate, "ox" denotes an oxalate, or ethanedioate, and ATFA@ denotes a trifluoroacetate.

* In the final column, the optical rotations of the compounds in salt form are given for (c=0.5, $H_2O$), the optical rotations of Compounds 3, 7, 8, 9 and 11 are given for (c=0.5, $CHCl_3$), the optical rotations of Compounds 15 and 16 are given for (c=0.5, $CH_2Cl_2$) and the optical rotations of compounds 18 to 36 are given for (c=0.5, $CH_3OH$).

TABLE

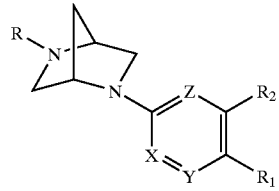

(1)

| No. | X | Y | Z | R | $R_1$ | $R_2$ | Salt | m.p. (° C.) | $[\alpha]_D^{20}$ (*) |
|---|---|---|---|---|---|---|---|---|---|
| 1 | CH | N | CH | H | H | H | HBr 2:1 | 268–270 | −103.2° |
| 2 | CH | N | CH | H | Cl | H | HCl 2:1 | 290–300 | −105.6° |
| 3 | CH | N | CH | $CH_3$ | H | H | — | oil | −126.7° |
| 4 | CH | N | CH | $CH_3$ | Cl | H | fum. 1:1 | 143.6 | −94.5° |
| 5 | N | CH | CH | H | Br | H | HCl 2:1 | 215–220 | −99.5° |
| 6 | N | N | CH | H | Cl | H | HCl 2:1 | 260–270 | −99.5° |
| 7 | N | N | CH | H | $C_6H_5$ | H | — | 162–163 | −187.8 |
| 8 | N | N | CH | $CH_3$ | $C_6H_5$ | H | — | 112.6–113 | −165.3 |
| 9 | CH | N | CH | H | H | $C_6H_5$ | — | 116–117 | −134.9 |
| 10 | N | CH | CH | H | $C_6H_5$ | H | HCl 2:1 | 192–205 | −108.1 |
| 11 | N | CH | CH | $CH_3$ | $C_6H_5$ | H | — | 45–50 | −170.4 |
| 12 | CH | N | CH | H | $OCH_3$ | H | HCl 2:1 | 188–190 | −85.7 |
| 13 | CH | N | CH | H | Br | H | fum. 1:1 | 199–202 | −81.8 |
| 14 | CH | N | CH | H | H | Br | fum. 1:1 | 225–230 | −76.5 |
| 15 | CH | N | CH | H | $C_6H_5$ | H | — | 121.5–122 | −178.7 |
| 16 | CH | N | CH | $CH_3$ | $C_6H_5$ | H | — | 86.5–87 | −174.1 |
| 17 | CH | N | CH | $CH_3$ | H | $C_6H_5$ | ox. 2:1 | 191–192 | −83.2 |
| 18 | CH | N | CH | H | H | 3,4-$OCH_2O$—$C_6H_3$ | TFA 2:1 | 150–151 | −68.5 |
| 19 | CH | N | CH | H | H | 3,5-$(CF_3)_2$—$C_6H_3$ | TFA 2:1 | 176–177 | −61.3 |
| 20 | CH | N | CH | H | H | 3-Cl—$C_6H_4$ | HBr 3:1 | 280 | −70.5 |
| 21 | CH | N | CH | H | H | 2,4-$Cl_2$—$C_6H_3$ | TFA 2:1 | 128–129 | −63.0 |
| 22 | CH | N | CH | H | H | 4-$CH_3O$—$C_6H_4$ | TFA 2:1 | 127–128 | −69.0 |
| 23 | CH | N | CH | H | H | 4-$CF_3$—$C_6H_4$ | TFA 2:1 | 189–190 | −65.0 |
| 24 | CH | N | CH | H | H | 4-$CH_3$—$C_6H_4$ | TFA 2:1 | 160–161 | −71.5 |
| 25 | CH | N | CH | H | H | 3-Cl, 4-F-$C_6H_3$ | TFA 2:1 | 150 | −67.7 |
| 26 | CH | N | CH | H | H | 4-F—$C_6H_4$ | HBr 2:1 | >280 | −76.2 |
| 27 | CH | N | CH | H | H | 3-$CH_3CO$—$C_6H_4$ | HBr 2:1 | >280 | −79.1 |
| 28 | CH | N | CH | H | H | 2-$CH_3$—$C_6H_4$ | TFA 2:1 | 157 | −70.8 |
| 29 | CH | N | CH | H | H | 2-$CH_3O$—$C_6H_4$ | TFA 2:1 | 134 | −64.7 |
| 30 | CH | N | CH | H | H | 2-Cl—$C_6H_4$ | TFA 2:1 | 139–140 | −68.9 |
| 31 | CH | N | CH | H | H | 2,3-$Cl_2$—$C_6H_3$ | TFA 2:1 | 146–147 | −66.5 |
| 32 | CH | N | CH | H | H | 3,4-$Cl_2$—$C_6H_3$ | TFA 2:1 | 140 | −66.9 |
| 33 | CH | N | CH | H | H | 3-$CF_3$—$C_6H_4$ | TFA 2:1 | 126 | −70.2 |
| 34 | CH | N | CH | H | H | 3-$CH_3O$—$C_6H_4$ | HBr 2:1 | 235 | −76.3 |
| 35 | CH | N | CH | H | H | 3-$CF_3O$—$C_6H_4$ | TFA 2:1 | 165–166 | −63.0 |
| 36 | CH | N | CH | H | H | 4-$CH_3S$—$C_6H_4$ | TFA 2:1 | 113 | −66.7 |
| 37 | CH | N | CH | $CH_3$ | 4-F—$C_6H_4$ | H | | | |
| 38 | CH | N | CH | $CH_3$ | 4-$CH_3O$—$C_6H_4$ | H | | | |
| 39 | CH | N | CH | $CH_3$ | 2-$CH_3O$—$C_6H_4$ | H | | | |
| 40 | CH | N | CH | $CH_3$ | 2-F—$C_6H_4$ | H | | | |

TABLE-continued

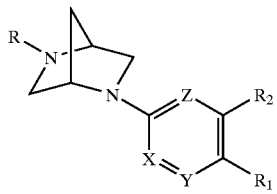

(1)

| No. | X | Y | Z | R | $R_1$ | $R_2$ | Salt | m.p. (° C.) | $[\alpha]_D^{20}$ (*) |
|---|---|---|---|---|---|---|---|---|---|
| 41 | CH | N | CH | $CH_3$ | 3-$CH_3$—$C_6H_4$ | H | | | |
| 42 | CH | N | CH | $CH_3$ | 3-$CH_3CO$—$C_6H_4$ | H | | | |
| 43 | CH | N | CH | $CH_3$ | 3-$CF_3$—$C_6H_4$ | H | | | |
| 44 | CH | N | CH | $CH_3$ | 4-$CF_3$—$C_6H_4$ | H | | | |
| 45 | CH | N | CH | $CH_3$ | 3,4-$(CH_3O)_2$—$C_6H_3$ | H | | | |
| 46 | CH | N | CH | $CH_3$ | 2,4-$(CH_3O)_2$—$C_6H_3$ | H | | | |
| 47 | CH | N | CH | $CH_3$ | 3-$CH_3O$—$C_6H_4$ | H | | | |
| 48 | CH | N | CH | $CH_3$ | 3,4-$OCH_2O$—$C_6H_3$ | H | | | |
| 49 | CH | N | CH | $CH_3$ | 4-$CH_3$—$C_6H_4$ | H | | | |
| 50 | CH | N | CH | $CH_3$ | 3-F—$C_6H_4$ | H | | | |
| 51 | CH | N | CH | $CH_3$ | 4-$CH_3CH_2$—$C_6H_4$ | H | | | |
| 52 | CH | N | CH | $CH_3$ | 4-F, 3-Cl—$C_6H_3$ | H | | | |

The compounds of the invention underwent tests which demonstrated their therapeutic properties.

Thus, they were studied as regards their affinity with respect to nicotinic receptors containing the $\alpha_4\beta_2$ subunit according to the methods described by Anderson and Arneric, Eur. J. Pharmacol (1994) 253 261, and by Hall et al., Brain Res. (1993) 600 127.

Male Sprague Dawley rats weighing 150 to 200 g are decapitated and the entire brain is removed quickly, homogenized in 15 volumes of 0.32 M sucrose solution at 4° C. and then centrifuged at 1000×g for 10 min. The pellet is discarded and the supernatant is centrifuged at 20,000×g for 20 min at 4° C. The pellet is recovered and homogenized using a Polytron™ mill in 15 volumes of double-distilled water at 4° C., followed by centrifugation at 8000×g for 20 min. The pellet is discarded and the supernatant and the "buffy coat" are centrifuged at 40,000×g for 20 min, the pellet is recovered, resuspended in 15 ml of double-distilled water at 4° C. and centrifuged again at 40,000×g, before being stored at −80° C.

On the day of the experiment, the tissue is thawed slowly and suspended in 3 volumes of buffer. 150 μl of this membrane suspension are incubated at 4° C. for 120 min in the presence of 100 μl of 1 nM [$^3$H]cytisine in a final volume of 500 μl of buffer, in the presence or absence of test compound. The reaction is stopped by filtration on Whatman GF/B™ filters pretreated with polyethyleneimine, the filters are rinsed with 2×5 ml of buffer at 4° C. and the radioactivity retained on the filter is measured by liquid scintigraphy. The non-specific binding is determined in the presence of 10 μM (−)-nicotine; the non-specific binding represents 75 to 85% of the total binding recovered on the filter. For each concentration of test compound, the percentage of inhibition of the specific binding of [$^3$H]cytisine is determined, followed by calculating the $IC_{50}$ value, which is the concentration of compound which inhibits the specific binding by 50%.

The $IC_{50}$ values for the purest compounds of the invention is between 0.001 and 0.25 μM.

The compounds of the invention were also studied as regards their affinity with respect to nicotinic receptors containing the α7 subunit, according to the methods described by Marks and Collins, J. Pharmacol. Exp. Ther. (1982) 22 554 and Marks et al., Mol. Pharmacol. (1986) 30 427.

Male OFA rats weighing 150 to 200 g are decapitated, the entire brain is removed quickly and homogenized using a Polytron™ mill in 15 volumes of a 0.32 M sucrose solution at 4° C., followed by centrifugation at 1000×g for 10 min. The pellet is discarded and the supernatant is centrifuged at 8000×g for 20 min at 4° C. The pellet is recovered and homogenized using a Polytron™ mill in 15 volumes of double-distilled water at 4° C., followed by centrifugation at 8000×g for 20 min. The pellet is discarded and the supernatant and the buffy coat are centrifuged at 40,000×g for 20 min. The pellet is recovered, resuspended with 15 volumes of double-distilled water at 4° C. and centrifuged again at 40,000×g for 20 min, before storing it at −80° C.

On the day of the experiment, the tissue is thawed slowly and suspended in 5 volumes of buffer. 150 μl of this membrane suspension is preincubated at 37° C. for 30 min, in the dark, in the presence or absence of the test compound. Next, the membranes are incubated for 60 min at 37° C., in the dark, in the presence of 50 μl of 1 nM [$^3$H]α-bungarotoxin in a final volume of 250 μl of 20 mM HEPES, 0.05% polyethyleneimine buffer. The reaction is stopped by filtration through Whatman GF/C™ filters pretreated for 3 hours with 0.5% polyethyleneimine. The filters are rinsed with 2×5 ml of buffer at 4° C. and the radioactivity retained on each filter is measured by liquid scintigraphy. The non-specific binding in the presence of α-bungarotoxin at 1 μM final is determined; the non-specific binding represents about 60% of the total binding recovered on the filter. For each concentration of test compound, the percentage of inhibition of the specific binding of [$^3$H]α-bungarotoxin is determined, followed by calculating the $IC_{50}$ value, which is the concentration of compound which inhibits the specific binding by 50%.

The $IC_{50}$ values for the purest compounds of the invention are between 0.005 and 0.6 μM.

The compounds of the invention were also studied as regards their affinity with respect to peripheral nicotinic receptors of ganglion type, according to the method described by Houghtling et al., Mol. Pharmacol. (1995) 48 280–287. The capacity of a compound to displace [$^3$H]- epibatidine from bovine adrenal gland membranes measures its affinity for this receptor.

Bovine adrenal glands stored at −80° C. are thawed and homogenized using a Polytron™ mill, in 20 volumes of 50 mM Tris-HCl buffer at pH 7.4 at 4° C., followed by centrifugation at 35,000×g for 10 min. The supernatant is discarded and the pellet is resuspended in 30 volumes of 50 mM Tris-HCl buffer at 4° C. and re-homogenized, after which it is recentrifuged at 35,000×g for 10 min. The final pellet is taken up in 10 volumes of Tris-HCl buffer at 4° C. 100 μl of membrane, i.e. 10 mg of fresh tissue, are incubated at 24° C. for 3 h in the presence of 50 μl of 0.66 nM final [$^3$H]-epibatidine in a final volume of 250 μl of buffer, in the presence or absence of test compound. The reaction is stopped by diluting the samples with 50 μM Tris-HCl buffer at pH 7.4 at 4° C., followed by filtration on Whatman GF/C™ filters pretreated for 3 hours with 0.5% polyethyleneimine. The filters are rinsed twice with 5 ml of buffer and the radioactivity retained on the filter is measured by liquid scintigraphy. The non-specific binding is determined in the presence of 2 mM final (−)-nicotine; the non-specific binding represents 30 to 40% of the total binding recovered on the filter. For each concentration of test compound, the percentage of inhibition of the specific binding of [$^3$H]-epibatidine is determined, followed by calculating the IC$_{50}$ value, which is the concentration of compound which inhibits the specific binding by 50%.

The IC$_{50}$ values for the compounds of the invention are between 0.1 and 20 μM.

The results of the preceding tests show that certain compounds of the invention are selective ligands for the α$_4$β$_2$, α$_7$ or α$_3$ subunits of the nicotinic receptor and that others are mixed α$_4$β$_2$ and α$_7$, α$_4$β$_2$ and α$_3$, or α$_7$ and α$_3$.

Finally, the compounds of the invention underwent tests which demonstrated their analgesic properties. Thus, they were studied in the hotplate model, according to the method by Eddy and Leimbach, *J. Pharmacol. Exp. Ther.* (1953) 107 385–393 with the aim of investigating and quantifying any analgesic effect. Mice weighing 20 to 30 g are subjected to a heat stimulus by contact of the paws with a plate kept at a constant temperature of 57.5° C. by a thermostatically controlled water bath. The reaction time to the pain, which is manifested by licking of the paws or jumping, is measured. Thus, after the interval of pretreatment carried out subcutaneously or orally (each batch consisting of eight animals for the same pretreatment), the mice are placed individually on the plate and the reaction time to the pain is measured. The animal is removed from the plate immediately after manifestation of the pain. The maximum exposure time to the stimulus is 30 seconds.

The mean reaction time and the standard error of mean (s.e.m.) are expressed for each batch. A non-parametric variance analysis (Kruskal-Wallis) is carried out on the entire batch. A Wilcoxon test allows comparison of each treated batch with the control batch. The differences are considered as statistically significant at the 5% threshold.

This reaction time is significantly increased by the analgesics mainly with central effects.

The compounds of the invention show activity in this test at doses of between 0.3 and 30 mg/kg intraperitoneally or orally.

The results of the various tests suggest the use of the compounds in the treatment or prevention of disorders associated with a dysfunction of the nicotinic receptors, in particular on the central nervous system or the gastrointestinal system.

On the central nervous system, these disorders comprise cognitive impairment, more specifically memory impairment, but also attention impairment, associated with Alzheimer's disease, pathological ageing (Age Associated Memory Impairment, AAMI), Parkinson's disease, trisomy 21 (Down's syndrome), Korsakoff's alcoholic syndrome, vascular dementia (multi-infarct dementia, MID) and attention deficit/hyperactivity disorder, ADHD).

The compounds of the invention may also be useful in the treatment of the motor disorders observed in Parkinson's disease or other neurological diseases such as Huntington's chorea, Tourette's syndrome, tardive dyskinesia and hyperkinesia.

The compounds of the invention can also constitute a curative or symptomatic treatment for cranial or medullary accidents and traumas, cerebrovascular accidents and cerebral hypoxic episodes, as well as other acute or chronic neurodegenerative diseases.

They can be used in psychiatric pathologies: schizophrenia, depression, anxiety, panic attacks, compulsive and obsessive behaviour.

They can prevent the symptoms due to withdrawal from tobacco, from alcohol and from various substances which induce a dependence, such as cocaine, LSD, cannabis and benzodiazepines.

Finally, they can be useful for the treatment of acute and neuropathic pain.

On the gastrointestinal system, the compounds of the invention may be useful in the treatment of Crohn's disease, ulcerous colitis, irritable bowel syndrome and obesity.

To this end, the compounds of the invention can be in any composition form which is suitable for enteral, parenteral or transdermal administration, such as tablets, sugar-coated tablets, gel capsules, wafer capsules, drinkable or injectable suspensions or solutions such as syrups or ampules, transdermal patches, etc., combined with suitable excipients, and dosed to allow a daily administration of from 0.01 to 20 mg/kg.

What is claimed is:

1. A compound of formula (I)

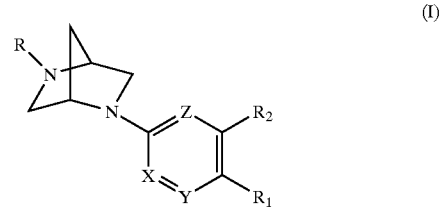

(I)

in which
one of the symbols X, Y and Z represents a nitrogen atom, another represents a group of formula C—R$_3$ and the third represents a nitrogen atom or a group of formula C—R$_4$, R$_3$ and R$_4$ represent, independently of each other, a hydrogen or halogen atom or a trifluoromethyl, cyano, hydroxyl, (C$_1$–C$_6$)alkyl or (C$_1$–C$_6$)alkoxy group, R$_1$ and R$_2$ represent, independently of each other, a hydrogen or halogen atom or a trifluoromethyl, cyano, hydroxyl, (C$_1$–C$_6$)alkyl or (C$_1$–C$_6$)alkoxy group, or a phenyl group optionally substituted with one or two halogen atoms, with one or two trifluoromethyl groups, with a cyano group, with a nitro group, with a hydroxyl group, with a (C$_1$–C$_6$)alkyl group, with one or two (C$_1$–C$_6$)alkoxy groups, with a methylenedioxy group, with an acetyl group, with a trifluoromethoxy group or with a methylthio group, R represents a hydrogen atom or a $(C_1–C_6)$alkyl group, with the exclusion of the compounds of formula (I) in which
   (a) Y and Z each represent a nitrogen atom,
   (b) X and Z represent a nitrogen atom, Y represents a group CH, R and $R_2$ are hydrogen and $R_1$ is fluorine,
   (c) X represents a nitrogen atom, Z represents a group $C(OCH_3)$, Y represents a group CH, and R, $R_1$ and $R_2$ are hydrogen, or
   (d) X represents a nitrogen atom, Z represents a group CH, Y represents a group CCl, and R, $R_1$ and $R_2$ are hydrogen
in base form or in the form of an addition salt with an acid.

2. A compound according to claim 1 wherein the heterocycle containing X, Y and Z is a 3-pyridyl group.

3. A compound according to claim 1 wherein the heterocycle containing X, Y and Z is a 3-pyridazinyl group.

4. A method for the treatment of disorders associated with a dysfunction of the nicotinic receptors which comprises administering to a patient in need of such treatment an effective amount of a compound according to any one of claims 1 to 3.

5. A pharmaceutical composition which comprises a compound according to any one of claims 1 to 3 together with an excipient.

* * * * *